United States Patent [19]

Takatsuka et al.

[11] Patent Number: 5,348,738
[45] Date of Patent: Sep. 20, 1994

[54] ORAL COMPOSITION WITH ACTIVE WATER INSOLUBLE POLYMER

[75] Inventors: Tsutomu Takatsuka; Shigeki Mori; Chiho Makino, all of Osaka, Japan

[73] Assignee: Sunstar Kabushiki Kaisha, Japan

[21] Appl. No.: 6,308

[22] Filed: Jan. 22, 1993

[30] Foreign Application Priority Data

Jan. 27, 1992 [JP] Japan ................................. 4-011887

[51] Int. Cl.$^5$ ..................... A61K 31/785; A61K 7/16; A61K 7/22
[52] U.S. Cl. ................................. 424/78.37; 424/49; 424/78.36
[58] Field of Search ..................... 424/49, 78.37, 78.08, 424/78.02, 78.36, 78.38

[56] References Cited

U.S. PATENT DOCUMENTS 5,063,046  11/1991  Grollier ........................... 424/78.08

FOREIGN PATENT DOCUMENTS

| | | |
|---|---|---|
| 0409670 | 1/1991 | European Pat. Off. . |
| 2113845 | 6/1972 | France . |
| 61-246205 | 11/1986 | Japan . |
| 649209 | 1/1987 | Japan . |
| 62-41641 | 9/1987 | Japan . |
| 64-26610 | 1/1989 | Japan . |
| 8301002 | 3/1983 | World Int. Prop. O. . |

OTHER PUBLICATIONS

Derwent Publications Ltd., Database WPIL, Section Ch, Week 8343, Class A97 (T. Matsumoto), Mar. 10, 1982.

*Primary Examiner*—Thurman K. Page
*Assistant Examiner*—William E. Benston, Jr.
*Attorney, Agent, or Firm*—Wegner, Cantor, Mueller & Player

[57] ABSTRACT

There is disclosed an oral composition comprising a water-insoluble polymer having quaternary nitrogen atoms as an active component and a polyoxyethylene-polyoxypropylene block copolymer surfactant as a stabilizing agent for the polymer. This composition has high adsorbability of microorganisms in the oral cavity and removes the microorganisms to exhibit improved dental plaque control effect.

14 Claims, No Drawings

ORAL COMPOSITION WITH ACTIVE WATER INSOLUBLE POLYMER

FIELD OF THE INVENTION

The present invention relates to an oral composition such as a dental composition. Specifically, the composition of the present invention adsorbs and removes microorganisms in the oral cavity to exhibit improved dental plaque control effect.

BACKGROUND OF THE INVENTION

It is known that a water-insoluble polymer having quaternary nitrogen atoms in its molecule (hereinafter referred to as a quaternary nitrogen-containing polymer) adsorbs microorganisms to exhibit antimicrobial activity. For example, JP-A 58-154502 and JP-A 64-26610 disclose the use of such a quaternary nitrogen-containing polymer as an agent for preventing and removing microorganisms and a bactericide of drinking water, cooling water and the like However, the application of the quaternary nitrogen-containing polymer to oral compositions has not yet been proposed in the field of oral hygiene.

When the quaternary nitrogen-containing polymer is used in oral compositions, since this kind of polymer is cationic, there is a problem that the polymer reacts with normally formulating anionic components such as foaming agents, binders or the like, and thereby significantly decreases in its antimicrobial activity. Therefore, in order to use the quaternary nitrogen-containing polymer in oral compositions, it is necessary to take measures to stabilize it.

OBJECTS OF THE INVENTION

The main object of the present invention is to provide an oral composition which adsorbs and removes microorganisms in the oral cavity to exhibit excellent dental plaque control effect.

This object as well as other objects and advantages of the present invention will become apparent to those skilled in the art from the following description.

SUMMARY OF THE INVENTION

Under these circumstances, the present inventors have intensively studied to formulate a water-insoluble polymer having quaternary nitrogen atoms in its molecule, in a stable form, into oral compositions. As a result, it has been found that polyoxyethylene-polyoxypropylene block copolymer surfactants specifically stabilize the quaternary nitrogen-containing polymer. Thus, the present invention has been completed.

That is, the present invention provides an oral composition which comprises an active component a water-insoluble polymer having quaternary nitrogen atoms and as a stabilizing agent for the water-insoluble polymer a polyoxyethylene-polyoxypropylene block copolymer surfactant. The oral composition of the present invention has high adsorpability of microorganism, removes microorganisms in the oral cavity efficiently and prevents the accumulation and calcification of their products to exhibit excellent dental plaque control effect.

DETAILED DESCRIPTION OF THE INVENTION

As examples of the water-insoluble polymer having quaternary nitrogen atoms in its molecule, namely, the quaternary nitrogen-containing polymer, there are quaternary nitrogen-containing polymers of quaternary ammonium type, betaine type, pyridylpyridinium type, diamine type or ether type represented by the formula (I):

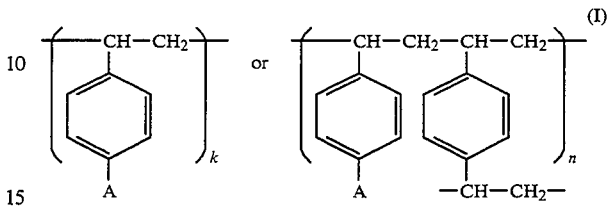

wherein A is

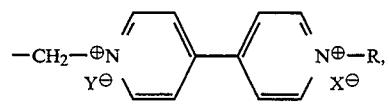

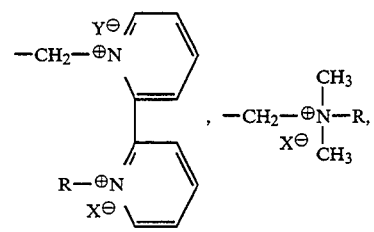

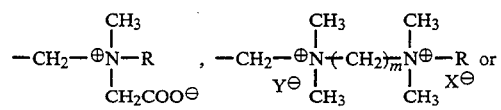

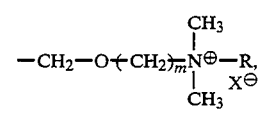

k is an integer of 20 to 2,000, n is an integer of not less than 10, preferably 10 to 10,000, X and Y are the same or different and are an anion such as a chloride ion or bromide ion, $R_1$ is alkyl having 6 to 18 carbon atoms and m is an integer of 2 to 10; and vinylpyridinium-type quaternary nitrogen-containing polymers having a repeating unit represented by the formula (II):

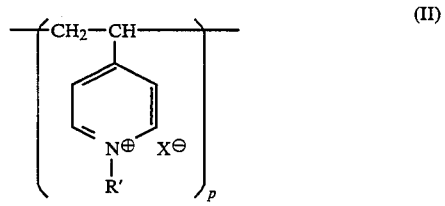

wherein R' is a group selected from the group consisting of benzyl, phenethyl, alkyl having 1 to 12 carbon atoms and pentafluorophenylmethyl, X is an anion such as a chloride ion or bromide ion and p is an integer of 20 to 3,000; or represented by the general formula (III):

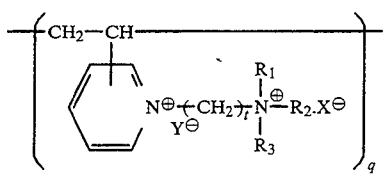

wherein $R_1$, $R_2$ and $R_3$ are the same or different and are selected from the group consisting of a hydrogen atom, a $C_{1-20}$ straight or branched chain saturated or unsaturated aliphatic hydrocarbon group (e.g., lauryl, oleyl, 2-methyldodecyl, 2-methyldodecenyl, etc.), hydroxyalkyl having 1 to 18 carbon atoms, alkoxyalkyl having 1 to 18 carbon atoms, aryloxyalkyl having 1 to 18 carbon atoms and trialkoxysilylaklyl whose alkoxy and alkyl having 1 to 18 carbon atoms, respectively, X and Y are the same or different and an anion such as a chloride ion or bromide ion, q is an integer of 20 to 2,500 and t is an integer of 1 to 20.

The typical molecular weight of the quaternary nitrogen-containing polymer is about 1,000 to 1,000,000, preferably about 5,000 to 800,000.

Examples of the quaternary nitrogen-containing polymer represented by the formula (I) include poly(vinylbenzylmethyllaurylammonium chloride), poly(vinylbenzylstearylbetaine), poly(vinylbenzyllaurylpyridylpyridinium chloride), poly(vinylbenzyllauryldiammonium chloride), poly(vinylbenzylcetylammonylhexyl ether) and the like.

The quaternary nitrogen-containing polymer can be prepared, for example, as follows:

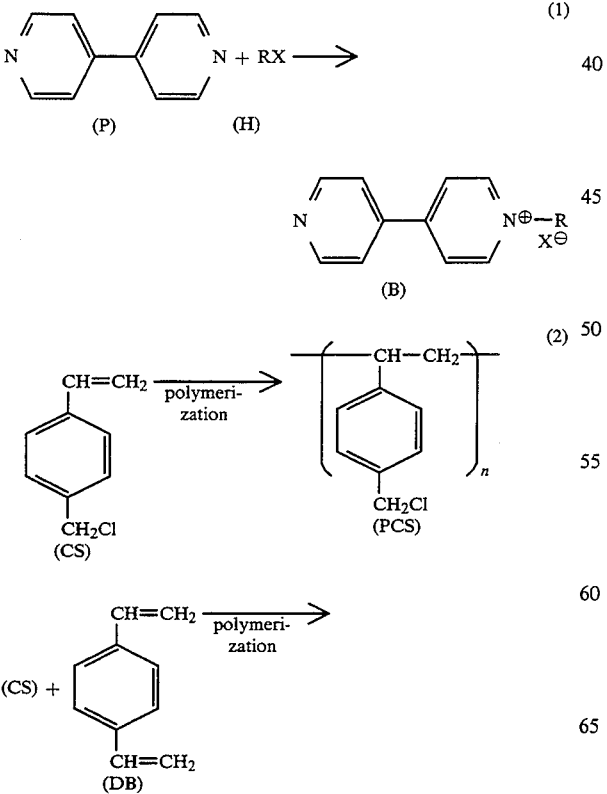

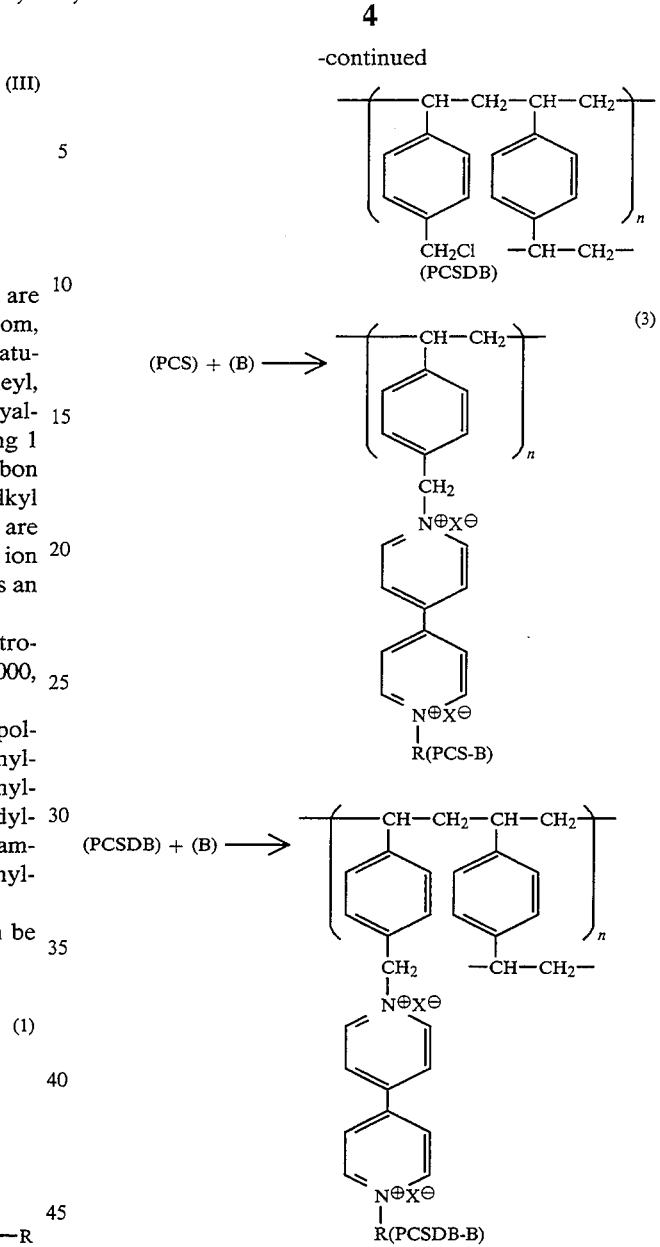

wherein each symbol is as defined above.

According to the reaction shown by the above reaction scheme (1), the product (B) is obtained. In this reaction, normally, the compound (H) is used in an amount of about 1.0 to 2.5 mol, preferably about 1.1 to 2.1 mol per 1 mol of the compound (P). The reaction is preferably carried out in an organic solvent such as methanol, ethanol, THF (tetrahydrofuran). In general, the reaction temperature is preferably about 60 to 110° C. The product (B) can be purified by conventional methods such as concentration, distillation, recrystallization and the like.

According to the reaction shown by the reaction scheme (2), the product (PCS) or (PCSDB) is obtained. The polymerization of the above reaction scheme (2) can be carried out by conventional methods such as suspension polymerization, solution polymerization, bulk polymerization and the like. The polymer thus obtained can be purified by conventional methods such as reprecipitation, washing and the like.

The reaction shown by the above reaction scheme (3) is carried out to obtain the desired microorganism-adsorbing polymer (PCS-B) or (PCSDB-B). In the reaction scheme (3), normally, the compound (B) is used in an amount of about 0.02 to 0.15 equivalents, preferably about 0.05 to 0.10 equivalents per 1 equivalent of the chlorine of the compound (PCS) or (PCSDB). The reaction is preferably carried our in an organic solvent such as that exemplified with respect to the above reaction of the scheme (1). In general, the preferred reaction temperature is about 60° to 100° C.

The quaternary nitrogen-containing polymer wherein the substituent represented by A in the formula (I) is other than that exemplified in the above reaction schemes (1) to (3) can be prepared according to the same manner.

Examples of the quaternary nitrogen-containing polymer having the repeating unit represented by the formula (II) include poly crosslinked-N-benzyl-4-vinylpyridinium bromide, poly crosslinked-N-phenethyl-4-vinylpyridinium bromide, poly crosslinked-N-hexadecyl-4-vinylpyridinium bromide, poly crosslinked-N-pentafluorophenylmethyl-4-vinyl-pyridinium bromide and the like.

Examples of the quaternary nitrogen-containing polymer having a repeating unit represented by the general formula (III) include 1-(N-methyl-N-benzyldodecylammoniopropyl)-4-vinylpyridinium bromide and the like.

Such a quaternary nitrogen-containing polymer can be prepared by copolymerizing and crosslinking the corresponding vinylpyridine and polyfunctional vinyl monomer in each repeating unit according to known methods such as solution polymerization, suspension polymerization and the like.

For example, the quaternary nitrogen-containing polymer having the repeating unit represented by the formula (II) can be prepared as follows:

Firstly, vinylpyridine and a polyfunctional vinyl monomer are copolymerized in the presence or absence of other vinyl monomers capable of coplymerizing with them to obtain a copolymer. Then, a known alkylating agent is reacted with the copolymer to introduce a substituent onto the nitrogen atom.

Examples of the polyfunctional vinyl monomer include divinylbenzene; polyfunctional (meth)acrylates such as ethylene glycol di(meth)acrylate, butanedioldi(meth)acrylate, trimethylolpropanetri(meth)acrylate, pentaerythritoldi(meth)acrylate, pentaerythritoltetra(meth)acrylate, polyethylene glycol(meth)acrylate and the like; polyfunctional (meth)acrylamides such as methylenebis(meth)acrylamide, propylenebis(meth)acrylamide, N,N'-(1,2dihydroxyethylene)bis(meth)acrylamide, N,N'-(carboxymethylene)bis(meth)acrylamide and the like.

Examples of the alkylating agent include benzyl halides (e.g., benzyl chloride, benzyl bromide, benzyl iodide) and those having substituent(s) in the aromatic ring, phenylethyl halides (e.g., phenylethyl chloride, phenylethyl bromide, phenylethyl iodide) and those having substituent(s) in the aromatic ring, pentafluorophenyl halides (e.g., pentafluorophenylmethyl chloride, pentafluorophenylmethyl bromide, pentafluorophenylmethyl iodide), alkyl halides having 1 to 12 carbon atoms, disulfuric esters of alcohols having 1 to 12 carbon atoms, p-toluenesulfonic acid esters, trifluoromethanesulfonic acid esters and the like.

The quaternary nitrogen-containing polymer having repeating units represented by the formula (III) can be prepared as follows:

Firstly, a given vinylpyridine and polyfunctional vinyl monomer are copolymerized in the presence or absence of other vinyl monomers capable of copolymerizing with them to obtain a copolymer. Then, dihaloalkyl having 1 to 20 carbon atoms such as dichloroalkyl, dibromoalkyl or diiodoalkyl is reacted to introduce a haloalkyl group onto the nitrogen atom of the vinylpyridine ring. Further, a tertiary amine is reacted with this to obtain a quaternary ammonium salt.

As the polyfunctional vinyl monomer, there can be used the same polyfunctional vinyl monomers as those described above. As the tertiary amine, there can be used, for example, saturated or unsaturated aliphatic tertiary amines such as trimethylamine, triethylamine, methyldiethylamine, N-dodecyldimethylamine, N-dodecenyldimethylamine, N'-octyldimethylamine or the like; aromatic tertiary amines such as N-benzyldimethylamine, N-phenethylmethylamine or the like; oxyalkylamines such as tri(hydroxyethyl)amine, bis(hydroxyethyl)methylamine or the like; silylalkylamines such as N,N-dimethyl-3-trimethoxysilylpropylamine, N-methyl-N-ethyl-3-trimethoxysilylpropylamine or the like.

In the production of the oral composition of the present invention, the quaternary nitrogen-containing polymer may be formulated as it is or in the form of a complex wherein the surface of a water-insoluble base is coated with the polymer, or the polymer can be supported on the surface of a water-insoluble base. In the latter two cases, the water-insoluble base is not specifically limited. For example, there can be used, for example, calcium hydrogenphosphate, calcium carbonate, alumina, silica gel, zeolite, nylon, polystyrene, polyethylene, methyl polymethacrylate or the like. When the water-insoluble base is coated with the quaternary nitrogen-containing polymer, the base is normally in the form of granules or powder. When the quaternary nitrogen-containing polymer is supported, the base may be in any form such as granules, powder, lumps, fibers, woven fabric, unwoven fabric, films, sponge or the like. For example, crosslinked chloromethylstyrene/styrene copolymer polymer beads or the like can advantageously be used.

In order to coat the surface of the water-insoluble base with the quaternary nitrogen-containing polymer represented by the formula (I), for example, the reaction shown by the above reaction scheme (3) is carried out on the surface of the water-insoluble base to obtain the desired complex. When quaternary nitrogen-containing polymers wherein the substituent represented by A in the formula (I) is other than that illustrated by the reaction schemes (1) to (3) are used, coating can be carried out according to the same manner.

In order to coat the surface of the water-insoluble base with the quaternary nitrogen-containing polymer having the repeating unit represented by the formula (II) or (III), the copolymerization of vinylpyridine and polyfunctional vinyl monomers in the above preparation method of polymer is carried out on the surface of the water-insoluble base, followed by making the nitrogen of the pyridine moiety quaternary by using an alkylating agent according the same manner as above to obtain the desired complex.

In order to support the quaternary nitrogen-containing polymer having the repeating unit represented by the formula (II) or (III) on the surface of the water-insoluble base, for example, the following method can be employed. As the water-insoluble base, a molded material of water-insoluble polymers having an optionally introduced halomethyl group of the formula: $XCH_2-$ (wherein X is a chlorine atom, bromine atom or iodine atom) (hereinafter referred to as a halomethyl polymer molded material) is used. Vinylpyridine homopolymer or a copolymer of vinylpyridine and other monomers is supported on the water-insoluble base by the reaction between the halomethyl group of the halomethyl polymer molded material and the pyridine ring moiety of the vinylpyridine polymer giving the quaternary compound. Further, the unreacted pyridine moiety was made quaternary by the use of an alkylating agent such as that exemplified above.

The oral composition of the present invention can be prepared by formulating the resulting quaternary nitrogen-containing polymer, complex wherein the surface of the water-insoluble base is coated with the polymer, or the supported compound wherein the polymer is supported on the surface of the water-insoluble base in an amount of about 0.001 to 50% by weight, preferably 0.1 to 10% by weight in terms of the amount of the polymer based on the total weight of the composition. When the amount to be formulated is less than 0.001% by weight, satisfactory microorganism-adsorbing effect cannot be obtained. On the other hand, when it exceeds 50% by weight, properties of the composition become unstable.

In the oral composition of the present invention, the polyoxyethylene-polyoxypropylene block copolymer surfactant forms aqueous gels as well as it acts as a stabilizing agent for the above quaternary nitrogen-containing polymer. The surfactant is a known surfactant composed of polyoxyethylene-polyoxypropylene glycol and commercially available from BASF Corporation (U.S.A.) under a trade name of "PLURONIC". In general, the surfactant is chemically defined according to the molecular weight of its hydrophorbic portion composed of polyoxypropylene and the proportion (% by weight) of its hydrophilic portion composed of polyoxyethylene based on the total molecular weight. Preferred polyoxyethylene-polyoxypropylene glycol has the molecular weight of the hydrophorbic group (polyoxypropylene) of 1,400 to 4,000 and contains 30 to 80% by weight of the hydrophilic group (polyoxyethylene) based on the total molecular weight.

The polyoxyethylene-polyoxypropylene block copolymer surfactant is formulated in an amount of about 15 to 80% by weight, preferably 20 to 50% by weight based on the total weight of the composition. When the amount to be formulated is less than 15% by weight, solid-liquid separation is caused and the properties of the composition become unstable because of insufficient gelation. On the other hand, when the amount to be formulated exceeds 80% by weight, gelation is too strong to obtain a suitable viscosity as an oral composition.

The oral composition of the present invention is appropriately formulated depending upon its particular use, for example, for dentifrices, preparations for gingival massage, or the like. There can also be formulated polishing powder, foaming agents, flavors, thickeners, sweetening agent, other active components and the like so long as they dose not impair the advantages of the present invention. Further, the oral composition can be prepared in the form of toothpaste, ointments, pastes, liniments, creams or the like according to conventional methods.

For example, in the case of dentifrice, there can be formulated calcium secondary phosphate dihydrate or anhydride, calcium primary phosphate, calcium tertiary phosphate, calcium carbonate, calcium pyrophosphate, aluminium hydroxide, alumina, silicic acid anhydride, silica gel, aluminium silicate, insoluble sodium metaphosphate, magnesium tertiary phosphate, magnesium carbonate, calcium sulfate, poly(methyl methacrylate), bentonite, zirconium silicate, synthetic polymers or the like alone or in combination thereof. The amount to be formulated is normally 5.0 to 90% by weight based on the total weight of the composition. Particularly in the case of toothpaste, it is 5 to 60% by weight.

As the thickener, there can be formulated sorbit, glycerin, ethylene glycol, propylene glycol, 1,3-butylene glycol, polyethylene glycol, polypropylene glycol, xylit, maltit, lactit or the like alone or in combination thereof. The amount to be formulated is normally 5 to 70% by weight based on the total weight of the composition.

As the flavor, there can be formulated menthol, carboxylic acid, anethole, eugenol, methyl salicylate, limonene, ocimene, n-decylalcohol, citronellol, α-terpineol, menthyl acetate, citronellyl acetate, methyleugenol, cineole, linalol, ethyllinalol, vanillin, thymol, spearmint oil, peppermint oil, lemon oil, orange oil, sage oil, rosemary oil, cinnamon oil, pimento oil, cassia oil, pelilla oil, winter-green oil, clove oil, oil of eucalyptus or the like alone or in combination thereof. The amount to be formulated is about 0.1 to 10% by weight, preferably about 0.5 to 5% by weight based on the total amount of the composition.

As the sweetening agent, there can be formulated sodium saccharin, stevioside, neohesperidyldihydrocharcone, glycyrrhizine, perillartine, thaumatin, aspartylphenylalanylmethyl ester, p-methoxycinnamicaldehyde or the like in an amount of 0.01 to 1% by weight, preferably 0.05 to 0.5% by weight based on the total weight of the composition.

In the oral composition of the present invention, as a pharmacologically active component, there can be formulated bactericides (e.g., cetylpyridinium chloride, chlorohexidine salts, triclosan, etc.), enzymes (e.g., dextranase, amylase, protease, mutanase, lysozyme, lytic enzyme, etc.), alkaline metal monofluorophosphate (e.g., sodium monofluorophosphate, potassium monofluorophosphate, etc.), fluorides (e.g., sodium fluoride, stannous fluoride, etc.), tranexamic acid, epsilon-aminocapronic acid, aluminium chlorohydroxylallantoin, dihydrocholesterol, glycyrrhizine salts, glycyrrhetic acid, glycerophosphate, chlorophyll, sodium chloride, caropeptide, water-soluble inorganic phosphoric acid compounds alone or in combination thereof. The amounts of these pharmacologically active components to be formulated are the same as those in conventional oral compositions. Any person skilled in the art can appropriately determine the amounts depending upon a particular use of the composition.

As described above, according to the present invention, there is provided an oral composition having high adsorpability of microorganisms which can remove microorganisms in the oral cavity to exhibit improved dental plaque control effect.

The following examples and comparative examples further illustrate the present invention in detail but are not to be construed to limit the scope thereof.

All the percents (%) used in the examples and comparative examples are by weight unless otherwise stated.

EXAMPLES 1 TO 8 AND COMPARATIVE EXAMPLES 1 TO 4

The dentifrice compositions of Example 1 to 8 and Comparative examples 1 to 4 were prepared by using particles of the quaternary nitrogen-containing polymers shown in Table 1 and Table 2 and complexes (mean particle diameter: 30 μm, in each case) wherein the surface of the water-insoluble base such as calcium hydrogenphosphate, silica gel or the like was coated with the polymer, and by mixing them together with the other ingredients described in Table 3 with stirring according to conventional methods.

The bacteria-adsorbing ability of each dentifrice composition thus obtained was evaluated as follows. The results are shown in Table 3.

Evaluation Method of the Bacteria-adsorpability

1. Preparation of a solution of contact bacteria

*Streptococcus sobrinus* OMZ176 was cultivated in brain-heart-infusion liquid medium under anaerobic conditions at 37° C. for 20 hours followed by centrifugation (7,000 rpm, 10 minutes) to harvest the cells. The cells thus obtained were washed with sterilized physiological saline. The cells were suspended in sterilized physiological saline so that the concentration of bacteria became about $10^7$ cells/ml ($OD_{560}=0.02$). The suspension was used as the solution of contact bacteria.

2. Evaluation of the bacteria-adsorbing ability (Shake flask method)

A given amount of sample of a dentifrice composition was placed in a 100 ml Erlenmeyer flask, and dispersed well by adding sterilized water (36 ml). The Erlenmeyer flask was placed in an incubator at 37° C. The contact bacteria solution (4 ml) of the above 1 was added, and the resulting mixture was shaken at 120 strokes/minute for 3 minutes. Then the Erlenmeyer flask was taken out of the incubator. After standing for some time, the supernatant (1 ml) was taken and diluted with sterilized physiological saline. The diluted solution (0.1 ml) was spread on brain-heart-infusion agar plate and incubated under anaerobic conditions at 37° C. for 48 hours. Then the number of the resulting colonies was counted. Since one cell spread on the agar plate divides and grows to form one colony, if the number of the colonies is counted, the number of the living cells after contact with the dentifrice composition over 3 minutes can be determined.

The bacteria-adsorbing ratio (%) of the dentifrice composition was evaluated by the following equation. The dentifrice having the ratio of not less than 90% was judged to have excellent bacteria-adsorbing ability.

Bacteria-adsorbing ratio(%) = $(A-B) \times 100/A$ wherein A is the number of the initial living cells and B is the number of the living cells after contact for 3 minutes.

TABLE 1

| Polymer No. | Chemical formula of polymer | Water-insoluble base |
|---|---|---|
| Polymer 1 | 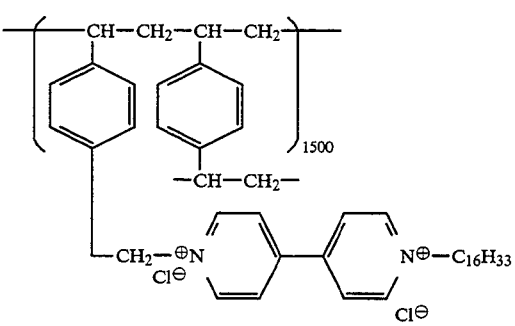 | None |
| Polymer 2 | 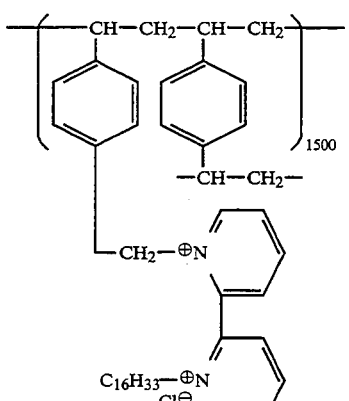 | None |

TABLE 1-continued
| Polymer No. | Chemical formula of polymer | Water-insoluble base |
|---|---|---|
| Polymer 3 | 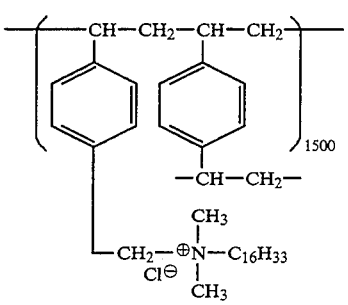 | None |
| Polymer 4 | 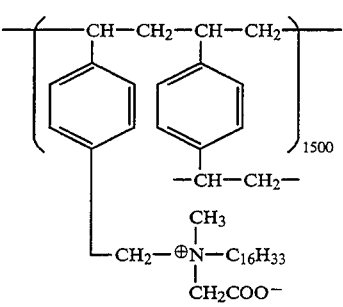 | None |
| Polymer 5 | 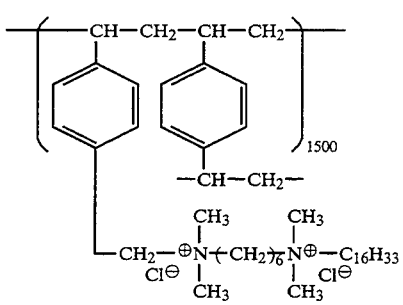 | None |
TABLE 2
| Polymer No. | Chemical formula of polymer | Water-insoluble base |
|---|---|---|
| Polymer 6 | 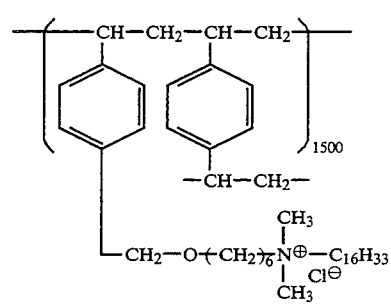 | None |

TABLE 2-continued

| Polymer No. | Chemical formula of polymer | Water-insoluble base |
|---|---|---|
| Polymer 7 | 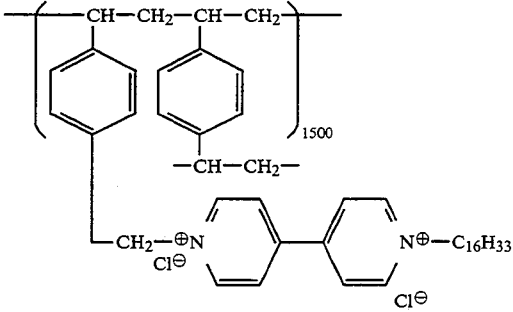 | Calcium hydrogen phospohate |
| Polymer 8 | 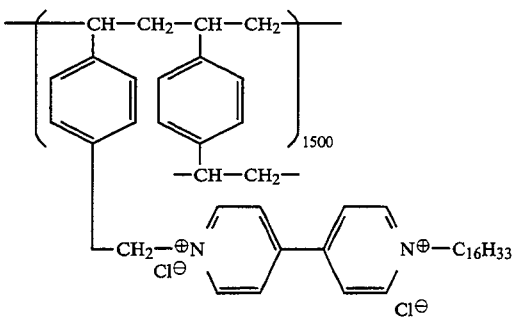 | Silica gel |
| Polymer 9 | 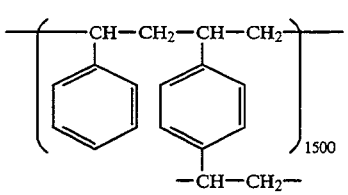 | None |

TABLE 3

| Ingredient | Example 1 | 2 | 3 | 4 | 5 | 6 | 7 | 8 | Comparative example 1 | 2 | 3 | 4 |
|---|---|---|---|---|---|---|---|---|---|---|---|---|
| Polymer 1 | 1.0 | — | — | — | — | — | — | — | — | 1.0 | 1.0 | — |
| Polymer 2 | — | 1.0 | — | — | — | — | — | — | — | — | — | — |
| Polymer 3 | — | — | 1.0 | — | — | — | — | — | — | — | — | — |
| Polymer 4 | — | — | — | 1.0 | — | — | — | — | — | — | — | — |
| Polymer 5 | — | — | — | — | 1.0 | — | — | — | — | — | — | — |
| Polymer 6 | — | — | — | — | — | 1.0 | — | — | — | — | — | — |
| Polymer 7 | — | — | — | — | — | — | 1.0 | — | — | — | — | — |
| Polymer 8 | — | — | — | — | — | — | — | 1.0 | — | — | — | — |
| Polymer 9 | — | — | — | — | — | — | — | — | 1.0 | — | — | — |
| Polyoxyethylene (194)[1] polyoxypropylene glycol (39)[1] | 30.0 | 30.0 | 30.0 | 30.0 | 30.0 | 30.0 | 30.0 | 30.0 | 30.0 | — | — | 30.0 |
| Polyoxyethylene-sorbitan monolaurate (20E.O.) | — | — | — | — | — | — | — | — | — | 30.0 | — | — |
| Sodium lauryl sulfate | — | — | — | — | — | — | — | — | — | — | 1.5 | — |
| Sodium carboxymethyl-cellulose | — | — | — | — | — | — | — | — | — | — | 1.5 | — |
| Calcium hydrogen-phosphate | 30.0 | 30.0 | 30.0 | 30.0 | 30.0 | 30.0 | 30.0 | 30.0 | 30.0 | 30.0 | 30.0 | 30.0 |
| Glycerine | 20.0 | 20.0 | 20.0 | 20.0 | 20.0 | 20.0 | 20.0 | 20.0 | 20.0 | 20.0 | 20.0 | 20.0 |
| Fravor | 1.0 | 1.0 | 1.0 | 1.0 | 1.0 | 1.0 | 1.0 | 1.0 | 1.0 | 1.0 | 1.0 | 1.0 |
| Sodium saccharin | 0.2 | 0.2 | 0.2 | 0.2 | 0.2 | 0.2 | 0.2 | 0.2 | 0.2 | 0.2 | 0.2 | 0.2 |
| Purified water | (balance) | | | | | | | | (balance) | | | |
| Total | 100.0 | 100.0 | 100.0 | 100.0 | 100.0 | 100.0 | 100.0 | 100.0 | 100.0 | 100.0 | 100.0 | 100.0 |
| Bacteria-adsorbing ratio (%) | 99.9 | 99.9 | 99.9 | 99.9 | 99.9 | 99.9 | 99.9 | 99.9 | 0 | 50.0 | 0 | 0 |

Note [1] The number in parenthesis indicates mean degree of polymerization.

As is clear from Table 3, the dentifrice compositions of Examples 1 to 8 each had an extremely excellent bacteria-adsorbing ratio of 99.9% because the quaternary nitrogen-containing polymers represented by the formula (I) were formulated into the compositions together with polyoxyethylene-polyoxypropylene block copolymer surfactants. Further, solid-liquid separation was not caused and the properties of the compositions were very stable.

On the other hand, the dentifrice composition of Comparative example 1 exhibited no bacteria-adsorbing effect because, although the same surfactant as that used in the above Example 1 to 8 was used, a polymer having no quaternary nitrogen in its molecule was formulated.

The dentifrice composition of Comparative example 2 and 3 did not exhibit good bacteria-adsorbing effect because, although a quaternary nitrogen-containing polymer was formulated, surfactants other than polyoxyethylene-polyoxypropylene block copolymer surfactants were used and thereby the quaternary nitrogen-containing polymer was not stabilized.

The dentifrice composition of Comparative example 4 exhibited no bacteria adsorbing effect because no polymer component was formulated into the composition.

From the above results, it is clear that the dentifrice compositions of Example 1 to 8 efficiently adsorb and remove oral bacteria because water-insoluble bacteria-adsorbing polymers having quaternary nitrogen atoms in its molecule are formulated together with surfactants which specifically stabilize the bacteria-adsorbing polymers and their antibacterial activity is not impaired.

EXAMPLE 9

Toothpaste was prepared by the following formulation according to a conventional method.

| Ingredient | Amount to be formulated (%) |
| --- | --- |
| Polymer 5 (Table 1) | 0.5 |
| Cetylpyridinium chloride | 0.1 |
| Sodium monofluorophosphate | 0.7 |
| PLURONIC F-88 (mean degree of polymerization: ethylene oxide 194 propylene oxide 39) | 30.0 |
| Calcium hydrogenphosphate | 20.0 |
| Glycerine | 20.0 |
| Flavor | 1.0 |
| Sodium saccharin | 0.2 |
| Purified water | balance |
| Total | 100.0 |

The bacteria-adsorbing ratio of the toothpaste thus obtained was evaluated according to the above method. As a result, excellent bacteria-adsorbing effect was observed

EXAMPLE 10

Cream for gingival massage was prepared by the following formulation according to a conventional method.

| Ingredient | Amount to be formulated (%) |
| --- | --- |
| Polymer 4 (Table 1) | 5.0 |
| Tocopheryl nicotinate | 0.5 |
| PLURONIC F-127 (mean degree of polymerization: ethylene oxide 196 propylene oxide 67) | 40.0 |
| Glycerine | 20.0 |
| Flavor | 0.6 |
| Dipotassium glycyrrhizate | 0.1 |
| Purified water | balance |
| Total | 100.0 |

The bacteria-adsorbing ratio of the cream for gingival massage thus obtained was evaluated according to the above method. As a result, excellent bacteria-adsorbing effect was observed.

EXAMPLES 11 TO 18 AND COMPARATIVE EXAMPLES 5 TO 8

By using the quaternary nitrogen-containing polymers listed in Table 4, complexes wherein the surface of the water-insoluble base such as silica gel, natural zeolite or the like was coated with the polymer and supported compound wherein the polymer was supported on the surface of crosslinked chloromethylstyrene/styrene copolymer polymer beads prepared as below, the dentifrice compositions of Examples 11 to 18 and Comparative examples 5 to 8 were prepared by mixing them together with the other ingredients listed in Table 4 with stirring.

The bacteria-adsorbing ability of each dentifrice composition thus obtained was evaluated according to the same manner as in the above Examples 1 to 8. The results are shown in Table 4.

Preparation of Crosslinked Chloromethylstyrene/styrene Copolymer Polymer Beads

Firstly, a solution composed of p-chloromethylstyrene (20 g), styrene (70 g), divinylbenzene (10 g) and lauroyl peroxide (1 g) and a solution composed of water (380 g) and polyvinylalcohol (23 g) (Gosenol GH-17, manufactured by Nihon Gosei Kagaku Kogyo Kabushiki Kaisha) were added to 1 liter separable flask equipped with a stirring apparatus, condenser, thermometer and nitrogen-introducing tube. Then, the mixed solution was heated at 80° C. for 8 hours with stirring at a rate of 200 rpm. The polymer beads thus obtained were separated by filtration, washed with water followed by acetone, dried in vacuo to obtain crosslinked chloromethylstyrene/styrene copolymer polymer beads. Yield: 95 g, the mean particle diameter of the polymer beads: 30 μm, chlorine content ratio: 4.6%.

TABLE 4

| Ingredient | Example | | | | | | | | Comparative example | | | |
| --- | --- | --- | --- | --- | --- | --- | --- | --- | --- | --- | --- | --- |
| | 11 | 12 | 13 | 14 | 15 | 16 | 17 | 18 | 5 | 6 | 7 | 8 |
| Polymer 10[2)] | 1.0 | — | — | — | — | — | — | — | — | 1.0 | 1.0 | — |
| Polymer 11[2)] | — | 1.0 | — | — | — | — | — | — | — | — | — | — |
| Polymer 12[2)] | — | — | 1.0 | — | — | — | — | — | — | — | — | — |
| Polymer 13[2)] | — | — | — | 1.0 | — | — | — | — | — | — | — | — |
| Polymer 14[2)] | — | — | — | — | 1.0 | — | — | — | — | — | — | — |
| Polymer 15[2)] | — | — | — | — | — | 1.0 | — | — | — | — | — | — |
| Polymer 16[2)] | — | — | — | — | — | — | 1.0 | — | — | — | — | — |

TABLE 4-continued

| Ingredient | Example | | | | | | | | Comparative example | | | |
|---|---|---|---|---|---|---|---|---|---|---|---|---|
| | 11 | 12 | 13 | 14 | 15 | 16 | 17 | 18 | 5 | 6 | 7 | 8 |
| Polymer 17[2)] | — | — | — | — | — | — | — | 1.0 | — | — | — | — |
| Polymer 18[2)] | — | — | — | — | — | — | — | — | 1.0 | — | — | — |
| Polyoxyethylene (194)[1)] polyoxypropylene glycol (39)[1)] | 30.0 | 30.0 | 30.0 | 30.0 | 30.0 | 30.0 | 30.0 | 30.0 | 30.0 | — | — | 30.0 |
| Polyoxyethylene-sorbitan monolaurate (20E.O.) | — | — | — | — | — | — | — | — | — | 30.0 | — | — |
| Sodium lauryl sulfate | | | | | | | | | | | 1.5 | |
| Sodium carboxymethyl-cellulose | — | — | — | — | — | — | — | — | — | — | 1.5 | — |
| Calcium hydrogen-phosphate | 30.0 | 30.0 | 30.0 | 30.0 | 30.0 | 30.0 | 30.0 | 30.0 | 30.0 | 30.0 | 30.0 | 30.0 |
| Glycerine | 20.0 | 20.0 | 20.0 | 20.0 | 20.0 | 20.0 | 20.0 | 20.0 | 20.0 | 20.0 | 20.0 | 20.0 |
| Fravor | 1.0 | 1.0 | 1.0 | 1.0 | 1.0 | 1.0 | 1.0 | 1.0 | 1.0 | 1.0 | 1.0 | 1.0 |
| Sodium saccharin | 0.2 | 0.2 | 0.2 | 0.2 | 0.2 | 0.2 | 0.2 | 0.2 | 0.2 | 0.2 | 0.2 | 0.2 |
| Purified water | (balance) | | | | | | | | (balance) | | | |
| Total | 100.0 | 100.0 | 100.0 | 100.0 | 100.0 | 100.0 | 100.0 | 100.0 | 100.0 | 100.0 | 100.0 | 100.0 |
| Bacteria-adsorbing ratio (%) | 99.9 | 99.9 | 98.0 | 99.9 | 97.0 | 95.0 | 98.0 | 96.0 | 0 | 40.0 | 0 | 0 |

Note) [1)]The number in the parenthesis indicates mean degree of polymerization.
[2)]Polymer 10 is poly crosslinked-N-benzyl-4-vinylpyridinium bromide, Polymer 11 is poly crosslinked-N-hexadecyl-4-vinyl-pyridinium bromide, Polymer 12 is poly crosslinked-N-pentafluorophenylmethyl-4-vinylpyridinium bromide, Polymer 13 is poly crosslinked-N-phenethyl-4-vinyl-pyridinium bromide, Polymer 14 is poly crosslinked-N-benzyl-4-vinylpyridinium bromide-silica gel complex, Polymer 15 is poly crosslinked-N-hexadecyl-4-vinylpyridinium bromide-natural zeolite complex, Polymer 16 is poly crosslinked-N-pentafluorophenylmethyl-4-vinylpyridinium bromide supported on crosslinked chloromethylstyrene/styrene copolymer polymer beads, Polymer 17 is poly crosslinked-N-phenethyl-4-vinyl-pyridinium bromide supported on crosslinked chloromethylstyrene/styrene copolymer polymer beads, and Polymer 18 is crosslinked chloromethylstyrene/styrene copolymer polymer beads.

Note) 1) The number in the parenthesis indicates mean degree of polymerization.

2) Polymer 10 is poly crosslinked-N-benzyl-4-vinyl-pyridinium bromide, Polymer 11 is poly crosslinked-N-hexadecyl-4-vinyl-pyridinium bromide, Polymer 12 is poly crosslinked-N-pentafluorophenylmethyl-4-vinyl-pyridinium bromide, Polymer 13 is poly crosslinked-N-phenethyl-4-vinylpyridinium bromide, Polymer 14 is poly crosslinked-N-benzyl-4-vinylpyridinium bromide-silica gel complex, Polymer 15 is poly crosslinked-N-hexadecyl-4-vinylpyridinium bromide-natural zeolite complex, Polymer 16 is poly crosslinked-N-pentafluorophenylmethyl-4-vinylpyridinium bromide supported on crosslinked chloromethylstyrene/styrene copolymer polymer beads, Polymer 17 is poly crosslinked-N-phenethyl-4-vinylpyridinium bromide supported on crosslinked chloromethylstyrene/styrene copolymer polymer beads, and Polymer 18 is crosslinked chloromethylstyrene/styrene copolymer polymer beads.

As is clear from Table 4, the dentifrice compositions of Examples 11 to 18 each had an extremely excellent bacteria-adsorbing ratio of 95.0% because the quaternary nitrogen-containing polymers represented by the formula (II) were formulated into the compositions together with polyoxyethylene-polyoxypropylene block copolymer surfactants. Further, solid-liquid separation was not caused and the properties of the compositions were very stable.

On the other hand, the dentifrice composition of Comparative example 5 exhibited no bacteria adsorption effect because, although the same surfactant as that used in the above Example 11 to 18 was used, a polymer having no quaternary nitrogen in its molecule was formulated.

The dentifrice composition of Comparative example 6 and 7 did not exhibit good bacteria adsorbing effect because, although the quaternary nitrogen-containing polymers were formulated, surfactants other than polyoxyethylene-polyoxypropylene block copolymer surfactants were used and thereby the quaternary nitrogen-containing polymer was not stabilized.

The dentifrice composition of Comparative example 8 exhibited no bacteria adsorbing effect because no polymer component was formulated into the composition.

From the above results, it is clear that the dentifrice compositions of Example 11 to 18 efficiently adsorb and remove oral bacteria because water-insoluble bacteria-adsorbing polymer having quaternary nitrogen atoms in its molecule are formulated together with surfactants which specifically stabilize the bacteria-adsorbing polymers and their antibacterial activity is not impaired.

EXAMPLE 19

Toothpaste was prepared by the following formulation according to a conventional method.

| Ingredient | Amount to be formulated (%) |
|---|---|
| Poly crosslinked-N-benzyl-pyridinium bromide | 0.5 |
| Cetylpyridinium chloride | 0.1 |
| Sodium monofluorophosphate | 0.7 |
| PLURONIC F-88 (mean degree of polymerization: ethylene oxide 194 propylene oxide 39) | 30.0 |
| Calcium hydrogenphosphate | 20.0 |
| Glycerine | 20.0 |
| Flavor | 1.0 |
| Sodium saccharin | 0.2 |
| Purified water | balance |
| Total | 100.0 |

The bacteria-adsorbing ratio of the toothpaste thus obtained was evaluated according to the above method. As a result, excellent bacteria adsorbing effect was observed.

EXAMPLE 20

Cream for gingival massage was prepared by the following formulation according to a conventional method.

| Ingredient | Amount to be formulated (%) |
| --- | --- |
| Poly crosslinked-N-hexadecyl-4-vinylpyridinium bromide | 5.0 |
| Tocopheryl nicotinate | 0.5 |
| PLURONIC F-127 (mean degree of polymerization: ethylene oxide 196 propylene oxide 67) | 40.0 |
| Glycerine | 20.0 |
| Flavor | 0.6 |
| Dipotassium glycyrrhizate | 0.1 |
| Purified water | balance |
| Total | 100.0 |

The bacteria-adsorbing ratio of the cream for gingival massage thus obtained was evaluated according to the above method. As a result, excellent bacteria-adsorbing effect was observed.

What is claimed is:

1. An oral composition comprising as an active component a water-insoluble polymer having quaternary nitrogen atoms and as a stabilizing agent for the polymer a polyoxyethylene-polyoxypropylene block copolymer surfactant, wherein the repeating unit of the water-insoluble polymer having quaternary nitrogen atoms is represented by the general formula (I):

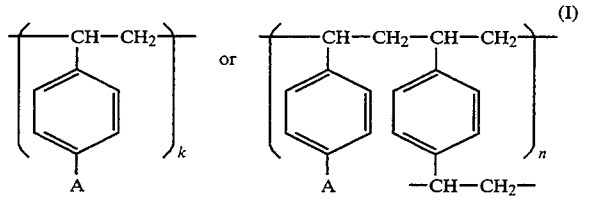

wherein A is

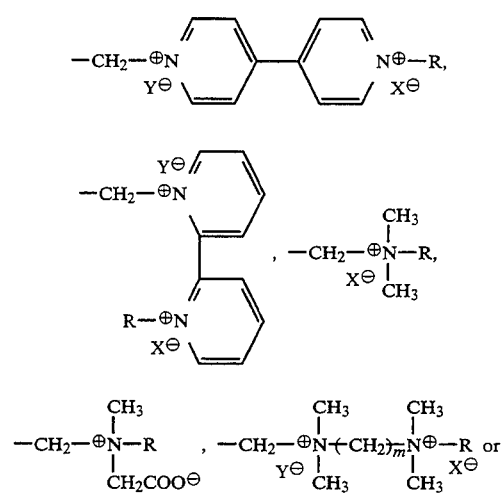

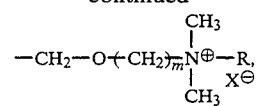

$k$ is an integer of 20 to 2,000, n is an integer of not less than 1,000, X and Y are the same or different and are an anion such as a chloride ion or bromide ion, $R_1$ is alkyl having 6 to 18 carbon atoms and m is an integer of 2 to 10; vinylpyridinium-type quaternary nitrogen-containing polymers having a repeating unit represented by the formula (II):

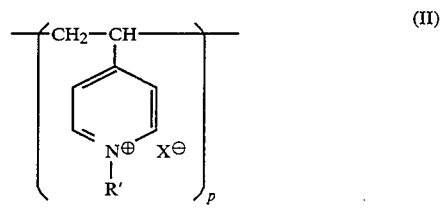

wherein R' is a compound selected from the group consisting of benzyl, phenethyl, alkyl having 1 to 12 carbon atoms and pentafluorophenylmethyl, X ia an anion such as a chloride ion or bromide ion and p is an integer of 20 to 3,000; or the general formula (III):

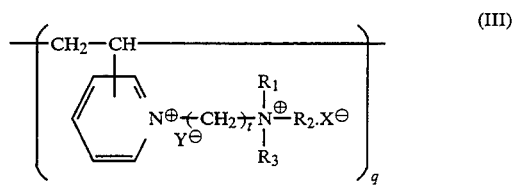

wherein $R_1$, $R_2$ and $R_3$ are the same or different and are selected from the group consisting of a hydrogen atom, a $C_{1-20}$ straight or branched chain saturated or unsaturated aliphatic hydrocarbon group, hydroxyalkyl, alkoxyalkyl, aryloxyalkyl and trialkoxysilylalkyl, X and Y are the same or different and an anion such as a chloride ion or bromide ion, q is an integer of 20 to 2,500 and t is an integer of 1 to 20.

2. An oral composition comprising as an active component a water-insoluble polymer having quaternary nitrogen atoms and as a stabilizing agent for the polymer a polyoxyethylene-polyoxypropylene block copolymer surfactant, wherein the repeating unit of the water-insoluble polymer having quaternary nitrogen atoms is represented by the general formula (I):

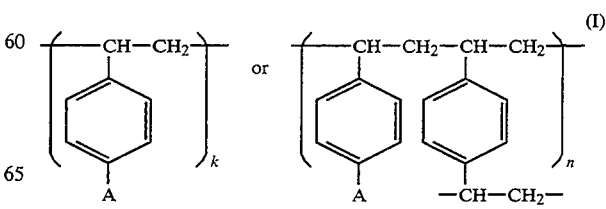

wherein A is

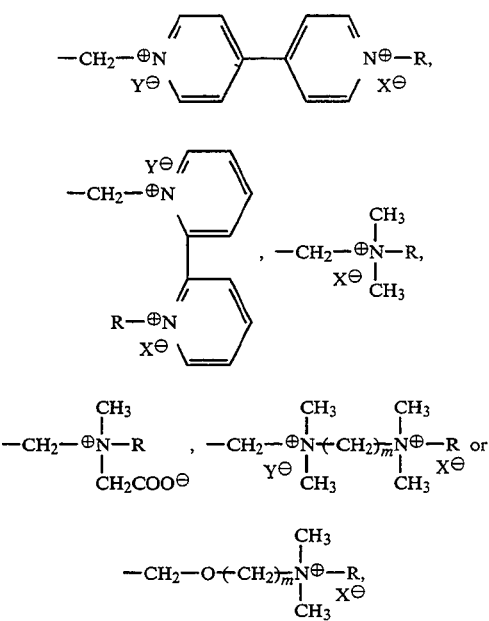

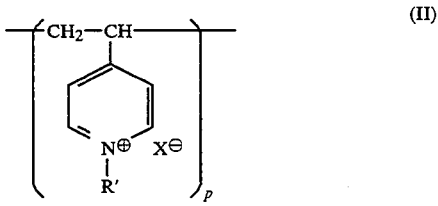

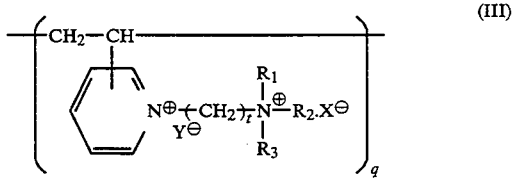

k is an integer of 20 to 2,000, n is an integer of not less than 10, X and Y are the same or different and are an anion such as a chloride ion or bromide ion, $R_1$ is alkyl having 6 to 18 carbon atoms and m is an integer of 2 to 10; vinylpyridinium-type quaternary nitrogen-containing polymers having a repeating unit represented by the formula (II):

$$\left(\text{CH}_2-\text{CH}\left(\text{C}_5\text{H}_4\text{N}^\oplus\text{R}'\right)\text{X}^\ominus\right)_p \quad \text{(II)}$$

wherein R' is a compound selected from the group consisting of benzyl, phenethyl, alkyl having 1 to 12 carbon atoms and pentafluorophenylmethyl, X ia an anion such as a chloride ion or bromide ion and p is an integer of 20 to 3,000; or the general formula (III):

$$\left(\text{CH}_2-\text{CH}\left(\text{C}_5\text{H}_4\text{N}^\oplus\text{Y}^\ominus(\text{CH}_2)_t\text{N}^\oplus\text{R}_1\text{R}_2\text{R}_3\cdot\text{X}^\ominus\right)\right)_q \quad \text{(III)}$$

wherein $R_1$, $R_2$ and $R_3$ are the same or different and are selected from the group consisting of a hydrogen atom, a $C_{1-20}$ straight or branched chain saturated or unsaturated aliphatic hydrocarbon group, hydroxyalkyl, alkoxyalkyl, aryloxyalkyl and trialkoxysilylalkyl, X and Y are the same or different and an anion such as a chloride ion or bromide ion, q is an integer of 20 to 2,500 and t is an integer of 1 to 20.

3. The oral composition according to claim 1, wherein the water-insoluble polymer having quaternary nitrogen atoms is selected from the group consisting of poly(vinylbenzylmethyllaurylammonium chloride), poly(vinylbenzylstearylbetaine), poly(vinylbenzyllaurylpyridylpyridinium chloride), poly(vinylbenzyllauryldiammonium chloride), poly(vinylbenzylcetylammonylhexyl ether), poly crosslinked-N-benzyl-4-vinylpyridinium bromide, poly crosslinked-N-phenethyl-4-vinylpyridinium bromide, poly crosslinked-N-hexadecyl-4-vinylpyridinium bromide, poly crosslinked-N-pentafluorophenylmethyl-4-vinylpyridinium bromide and 1-(N-methyl-N-benzyldodecylammoniopropyl)-4-vinylpyridinium bromide.

4. The oral composition according to claim 1, wherein the amount of the water-insoluble polymer having quaternary nitrogen is 0.001 to 50% by weight based on the total weight of the composition.

5. The oral composition according to claim 4, wherein the amount of the water-insoluble polymer having quaternary nitrogen atoms is 0.1 to 10% by weight based on the total weight of the composition.

6. The oral composition according to claim 1, wherein the polyoxyethylene-polyoxypropylene block copolymer surfactant is composed of polyoxyethylene-polyoxypropylene glycol having the molecular weight of the polyoxypropylene moiety of 1,400 to 4,000 and containing 30 to 80% by weight of the polyoxyethylene moiety based on the total molecular weight.

7. The oral composition according to claim 1, wherein the amount of the polyoxyethylene-polyoxypropylene block copolymer surfactant is 15 to 80% by weight based on the total weight of the composition.

8. The oral composition according to claim 1, wherein the amount of the polyoxyethylene-polyoxypropylene block copolymer surfactant is 20 to 50% by weight based on the total weight of the composition.

9. The oral composition according to claim 2, wherein n is an integer from 10 to 10,000.

10. The oral composition according to claim 2, wherein the amount of the water-insoluble polymer having quaternary nitrogen is 0.001 to 50% by weight based on the total weight of the composition.

11. The oral composition according to claim 10, wherein the amount of the water-insoluble polymer having quaternary nitrogen atoms is 0.1 to 10% by weight based on the total weight of the composition.

12. The oral composition according to claim 2, wherein the polyoxyethylene-polyoxypropylene block copolymer surfactant is composed of polyoxyethylene-polyoxypropylene glycol having the molecular weight of the polyoxypropylene moiety of 1,400 to 4,000 and containing 30 to 80% by weight of the polyoxyethylene moiety based on the total molecular weight.

13. The oral composition according to claim 2, wherein the amount of the polyoxyethylene-polyoxypropylene block copolymer surfactant is 15 to 80% by weight based on the total weight of the composition.

14. The oral composition according to claim 2 wherein the amount of the polyoxyethylene-polyoxypropylene block copolymer surfactant is 20 to 50% by weight based on the total weight of the composition.

* * * * *